United States Patent [19]

Haneline

[11] Patent Number: 5,048,541
[45] Date of Patent: Sep. 17, 1991

[54] X-RAY PATIENT RESTRAINT

[76] Inventor: Michael T. Haneline, 236 Jamacha Rd., El Cajon, Calif. 92019

[21] Appl. No.: 562,829

[22] Filed: Aug. 6, 1990

[51] Int. Cl.⁵ ............................................... A61F 5/37
[52] U.S. Cl. .................................... 128/876; 128/849; 128/846; 128/830; 128/842; 128/384; 128/385; 128/386
[58] Field of Search ............... 128/876, 384, 385, 386; 252/478; 250/515, 516, 519; 378/208, 209, 210

[56] References Cited

U.S. PATENT DOCUMENTS

| | | | |
|---|---|---|---|
| 2,912,977 | 11/1959 | Holbrook | 128/870 |
| 3,310,053 | 3/1967 | Greenwood | 250/516.1 X |
| 3,535,719 | 10/1970 | Murcott | 128/876 X |
| 4,779,858 | 10/1988 | Saussereau | 378/209 |
| 4,938,233 | 7/1990 | Orrison, Jr. | 250/516.1 X |

Primary Examiner—Robert A. Hafer
Assistant Examiner—Brian E. Hanlon
Attorney, Agent, or Firm—Ralph S. Branscomb

[57] ABSTRACT

An X-ray patient restraint comprises brackets which are mounted on the laterally opposite sides of the front of the backboard which also receives the X-ray film, and a restraint strap passes through the brackets to adjustably attach back to itself with Velcro (tm) fasteners. The preferred embodiment is quite wide in order to compress a wide area of the abdominal area of the patient against the backboard for greater print clarity, and two genital shields are alternately and removably attached with Velcro (tm) to cover the gonads or ovaries of the patient.

13 Claims, 1 Drawing Sheet

X-RAY PATIENT RESTRAINT

BACKGROUND OF THE INVENTION

X-ray stations are now common in tens or thousands of hospitals and doctors offices across the country. The instant invention pertains to an X-ray station which includes a vertical backboard against which the patient is pressed while the X-Ray photograph is made. Typically these X-rays are made of the chest to assess the condition of the lungs, and even more commonly, of the spinal column to access alignment, particularly in chiropractic offices.

The radiographic film is inserted in the backboard so that it is immediately behind the patient. The closer the film is to the boney structure that is being photographed the more crisp the final prints will be. Obviously, the crispness of the prints will also be a function of the degree to which the patient is able to remain motionless during the split second that the radiographic film is being irradiated.

Although there are a number of restraints which are used in surgery and for restraining a patient during X-Rays, often these are rather complicated in nature and are used for patients on X-ray tables. There is a need for a simple and effective restraint which is used on the vertical backboard type of X-ray station to maintain the area to be photographed as motionless as possible, and to compress it against the backboard to sharpen the resulting photograph images.

SUMMARY OF THE INVENTION

The instant invention fulfills the above stated need and comprises a restraint having a pair of brackets mounted on the lateral opposite side edges of the backboard, and a flexible strap which passes through these brackets in its end portions, and loops back to attach to its central regions with hook-and-loop fastener material.

In the preferred embodiment, the strap is very wide in its central portion, on the order of 6" to 12". This insures an even compression of the patient's body over a wide area against the backboard. A narrower alternate strap may also be provided for instances in which the patient must bend to one side during the X-ray session.

With either embodiment, two X-ray shield accessories are provided, one for men and one for women. Both comprise flexible members having lead pockets contained inside, and being alternatively and releasibly attached to the central portion of the strap with Velcro (tm). The men's version is suspended below the strap to cover the gonads, whereas the women's version includes two laterally extended ovary covers.

DESCRIPTION OF THE PREFERRED EMBODIMENT

Figure 1:
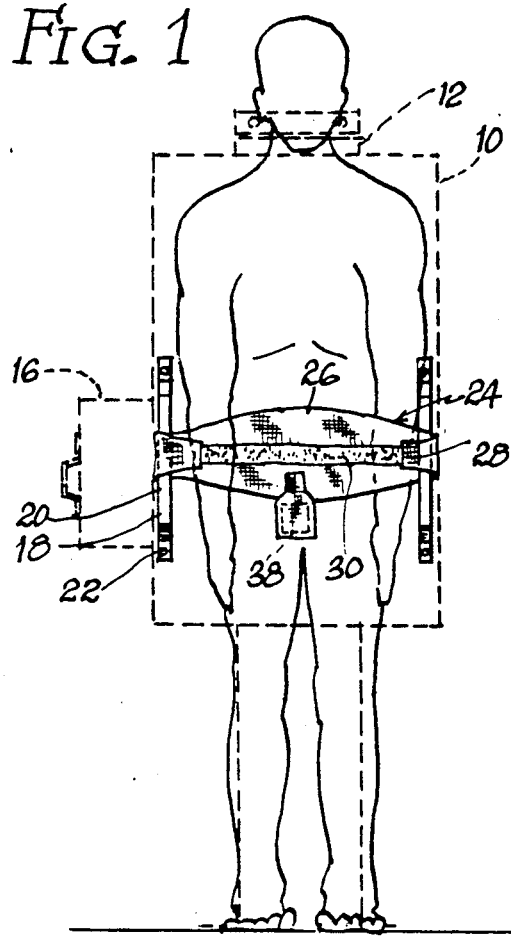
FIG. 1 illustrates the invention in use with a patient restrained against a backboard and indicating the location of a typical X-ray plate.
Figure 2:
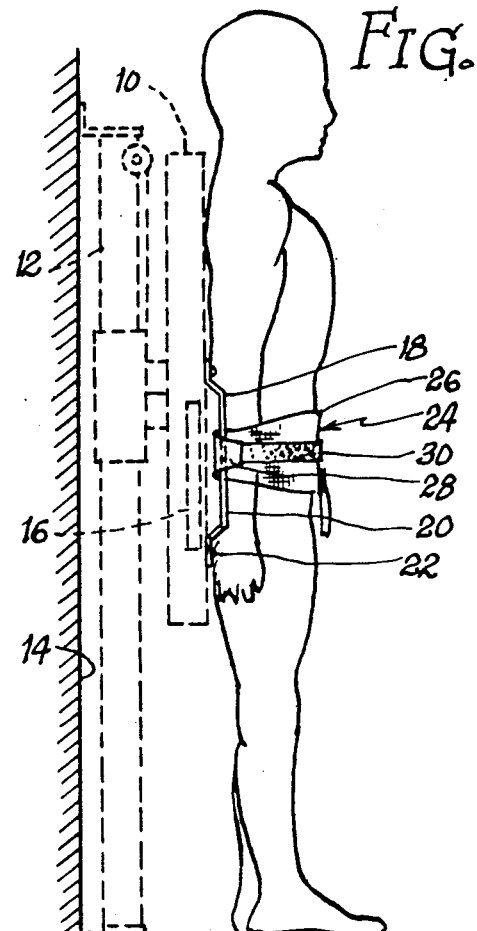
FIG. 2 is a side elevation view of the unit in use as shown FIG. 1.
Figure 3:
FIG. 3 is a front elevation view of the ovary shield.
Figure 4:
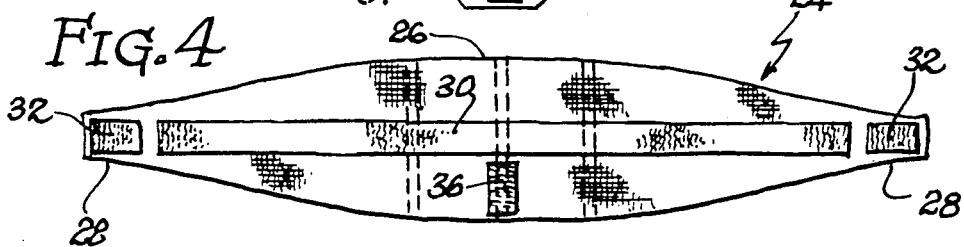
FIG. 4 is a front elevation view of the strap as it appears fully extended.
Figure 5:
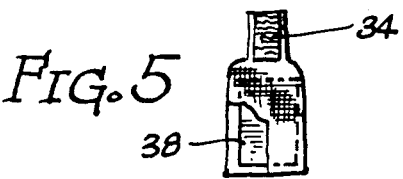
FIG. 5 is a front elevation view of the male gonad shield.

A patient is shown in FIGS. 1 and 2 pressed up against the backboard 10 of a typical X-Ray station. The backboard is vertically adjustable so that children, and different regions of the body can be photographed, and slides on a structure 12 something like that indicated in FIGS. 1 and 2. This structure is obviously very diagrammatically shown as it is not, by itself, part of the invention. The sliding structure is mounted against a backwall 14 or other support. The X-Ray plate 16 typically slides into a plateholder defined in the backboard.

The invention itself comprises a pair of brackets 18 which are illustrated as rails 20 bolted to the backboard at 22. These rails are spaced adequately to accommodate the torso of a patient as shown in FIG. 1. They would ordinarily lie just adjacent to lateral side edges of the backboard.

The strap 24, which is the part of the invention, has a wide central portion 26 in its preferred embodiment, and tapers down to ends 28 which will pass through the rails 20 of the brackets, and because the ends are narrower than the middle, vertical adjustment of the strap is easily permitted.

The strap is shown in the drawings as having an elongated patch 30 along its central portion, and patches 32 of the material which mates to the material 30 attached to the ends 28. The precise configuration of the Velcro is of course subject to some change, but the idea is that the ends pass through the brackets 18 and fasten to the central portions as best shown in FIGS. 1 and 2. Thus, the tightening adjustment of the strap is automatically provided, as well as its vertical adjustability within the brackets.

Although it would be possible to provide a strap having one end which is non-adjustably connected to a bracket or the like, with all of the tightening adjustment provided by the other end of the strap, this would tend to make it more difficult to center the patient on the backboard. When tightening one side only of the strap, the patient would be deflected somewhat to one side, which would be especially inappropriate if the patient were being examined for spinal curvature disorders such as Scoliosis.

Although the X-rays produced by X-ray machines are alleged to be too weak to cause cumulative damage such as increased Cancer risk, nonetheless California law requires these areas of the body which are most prone to X-ray damage, which are the gonads and testicles of the male, and the ovaries of the female, to be covered. Both the strap and the shields are made from any kind of fabric or flexible material desired, such as nylon fabric, but even lined Vinyl or cotton blends can be used. The shields have a Velcro patch 34 on the face which attaches to the strap, and the strap has a special patch 36, which could also be either an extension of the patch 26, or the shields could be modified to extend up to that patch. The shields also have the cover elements themselves, indicated at 38 and 40, which are made of lead plates or lead shot contained in pockets in the fabric of the shields.

The principle embodiment of the strap is from 6 to 12 inches wide so that a wide area of the abdomen is pressed against the backboard. This assures not only the maximum immobility of the patient's torso, but also presses a wide area uniformly against the backboard for an enhanced photographic image.

Figure 6:
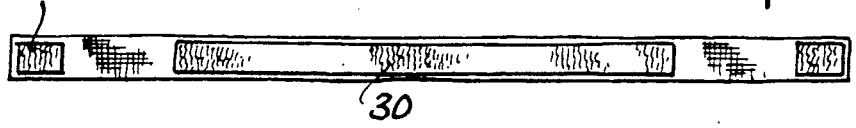
FIG. 6 is a front elevation view of a second embodiment of a narrower strap as it appears fully extended.

However, in some instances, the patient is required to bend over sideways as much as possible while the X-ray is taken so that the lateral flex of the spine can be studied. In this case, a wide strap would be an impediment, and a narrow strap such as that shown in FIG. 6 would be used instead. This strap may also be used with the convenient mating Velcro reproductive shields as described above.

In either embodiment, the restraint is very simple and requires only a minor modification of the X-ray station backboard. It has been successfully used by the inventor and produces a noticeable improvement in the quality of the X-ray photographs, which in turn improves the diagnostic and treatment capabilities of the physician or other health professional. In the overall scheme of improving medical technology, this invention represents an addition that is significant and yet is relatively inexpensive and simple enough to use that any technician with minimal training can take advantage of its benefits.

It is hereby claimed:

1. An X-ray patient restraint for restraining the patient against the substantially vertical film backboard of an upright X-ray station comprising:
    (a) a pair of brackets mounted to the laterally opposite sides of said backboard;
    (b) a restraint strap for extending across a patient positioned against said backboard;
    (c) fastener means to engage said strap to said brackets to hold said patient securely against said backboard;
    (d) said strap being elongated and having ends which respectively extend through said respective brackets, and said fastener means comprising detent structure on the ends of said strap which loop back from said brackets and attach to a central portion of said strap; and,
    (e) at least one genital shield for said strap, said genital shield being removably attachable to said strap and including releasible fastener means for attaching said shield to said strap.

2. Structure according to claim 1 wherein said detent means comprises hook-and-loop fastener material mounted to the ends of said strap which releasibly attach to mating hook-and-loop fastener material on the central portion of said strap.

3. Structure according to claim 1 wherein said strap has an expanded central portion on the order of 5 to 12 inches wide to compress a wide abdominal area of the patient against said backboard and converges to widths at its ends which are less than half of the width at said central portion.

4. Structure according to claim 3 wherein said releasible fastener means comprises mating hook-and-loop fastener material respectively attached to said strap and shield such that said shield depends from said strap in use.

5. Structure according to claim 4 and including two removable genital shields, the first having a depending gonad radiopaque cover and the second having laterally extended radiopaque ovary covers.

6. Structure according to claim 5 wherein said radiopaque covers comprise pockets of lead mounted in the respective shield.

7. Structure according to claim 1 wherein said brackets are forwardly extended on said backboard to permit the unobstructed loading and unloading of X-ray film into said backboard.

8. An X-ray patient restraint for temporarily immobilizing a patient while upright, comprising:
    (a) a backboard having means to support same substantially vertically;
    (b) a pair of brackets mounted to the respective opposite sides of said backboard;
    (c) a strap passing through said brackets;
    (d) detentes for temporarily detaining said straps in said brackets,
    (e) said strap having a central portion and ends which respectively mount matable hook-and-loop patches such that both of the ends of said strap pass through said brackets and engage the central portions thereof with the hook-and-loop fastener material; and
    (f) a plurality of interchangeable genital shields releasibly attachable to said strap.

9. Structure according to claim 8 wherein said brackets have forwardly projecting rails to engage said strap to avoid interference with any radioactive plate positioning in said backboard from the side of said backboard.

10. Structure according to claim 8 and including a male genital shield having lead pockets for covering the gonads and a female genital shield having lead pockets to cover the ovaries.

11. For an X-ray station having a film backboard with a pair of laterally spaced brackets positioned to accommodate the torso of a patient therebetween on said backboard, an X-ray patient restraint structure for retaining a patient against the backboard comprising:
    (a) a strap having an expanded central portion on the order of 5" to 12" wide and mounting a patch of hook-and-loop fastener material; and
    (b) said strap having two ends with patches of hook-and-loop fastener material such that said ends pass through said brackets and the patches thereon mate with the patch on said central portion to adjustably and releasibly restrain a patient; and,
    (c) at least one genital shield for said strap, said genital shield being removable and including releasible fastener means for attaching said shield to said strap.

12. Structure according to claim 11 wherein said releasible fastener means comprises mating hook-and-loop fastener material attached to said strap ends to mate with the patches on the central portion.

13. Structure according to claim 12 and including two removable genital shields, the first having a depending gonad radiopaque cover and the second having laterally extending ovary radiopaque covers.

* * * * *